US006894160B2

(12) United States Patent
Capan et al.

(10) Patent No.: US 6,894,160 B2
(45) Date of Patent: May 17, 2005

(54) CATALYTIC PROCESS FOR THE MODIFICATION OF CARBOHYDRATES, ALCOHOLS, ALDEHYDES OR POLYHYDROXY COMPOUNDS

(75) Inventors: Emine Capan, Braunschweig (DE); Marc Sascha Hahnlein, Mannheim (DE); Ulf Prusse, Braunschweig (DE); Klaus-Dieter Vorlop, Braunschweig (DE); Alireza Haji Begli, Ramsen (DE)

(73) Assignee: Sudzucker Aktiengesellschaft Mannheim/Ochsenfurt (DE)

( * ) Notice: Subject to any disclaimer, the term of this patent is extended or adjusted under 35 U.S.C. 154(b) by 0 days.

(21) Appl. No.: 10/340,913

(22) Filed: Jan. 10, 2003

(65) Prior Publication Data

US 2003/0139594 A1 Jul. 24, 2003

Related U.S. Application Data

(62) Division of application No. 09/936,891, filed on Oct. 19, 2001.

(30) Foreign Application Priority Data

Mar. 16, 1999 (DE) ........................................ 199 11 504

(51) Int. Cl.[7] .......................... C07H 5/04; C07C 29/26; C07C 29/14

(52) U.S. Cl. ................ 536/55.3; 536/1.11; 536/123.13; 536/124; 564/473; 568/863

(58) Field of Search .............................. 536/1.11, 55.3, 536/123.13, 124; 564/473; 568/863; 514/54; 502/185

(56) References Cited

U.S. PATENT DOCUMENTS 4,845,208 A * 7/1989 Fuertes et al. .............. 536/124
5,643,849 A 7/1997 Au ............................ 502/185

FOREIGN PATENT DOCUMENTS

| | | |
|---|---|---|
| DE | 198 03 891 | 8/1999 |
| EP | 0 201 957 | 11/1986 |
| EP | 0 665 265 | 8/1995 |
| EP | 0 857 748 | 8/1998 |
| EP | 0 879 642 | 11/1998 |
| WO | WO 97/34861 | 9/1997 |
| WO | WO 00/29332 | 5/2000 |

OTHER PUBLICATIONS

K. Kaneda, et al., "Catalysis of Giant Palladium Cluster Complexes, Highly Selective Oxidations of Primary Allylic Alcohols to $\alpha,\beta$–Unsaturated Aldehydes in the Presence of Molecular Oxygen", *Tetrahedron Letters*, vol. 38, No. 52, 1997, pp. 9023–9026.

U. Prüsse, et al., "Encapsulation of Microscopic Catalysts in Polymer Network Gels", *Chemie Ingenieur Technik*, 69 (1/2), pp. 100–103.

Crooks, R.M. "Homogeneous Hydrogenation Catalysis with Monodisperse Dendrimer–Encapsulated Pd and Pt Nanoparticles," angew. Chem. Int. Ed. 1999, 38(3), 364–365.

* cited by examiner

*Primary Examiner*—James O. Wilson
*Assistant Examiner*—Ganapathy Krishnan
(74) *Attorney, Agent, or Firm*—Ostrolenk, Faber, Gerb & Soffen, LLP

(57) ABSTRACT

The invention relates to the industrial conversion of carbohydrates, alcohols, aldehydes or polyhydroxy compounds in aqueous phase. According to the invention a catalytic method is used for the conversion, using a metal catalyst consisting of polymer-stabilized nanoparticles. A catalyst of this type is not deactivated by the conversion reaction as long as the stabilizing interaction between the polymer and the nanoparticles is maintained.

2 Claims, 7 Drawing Sheets

Figure 1:
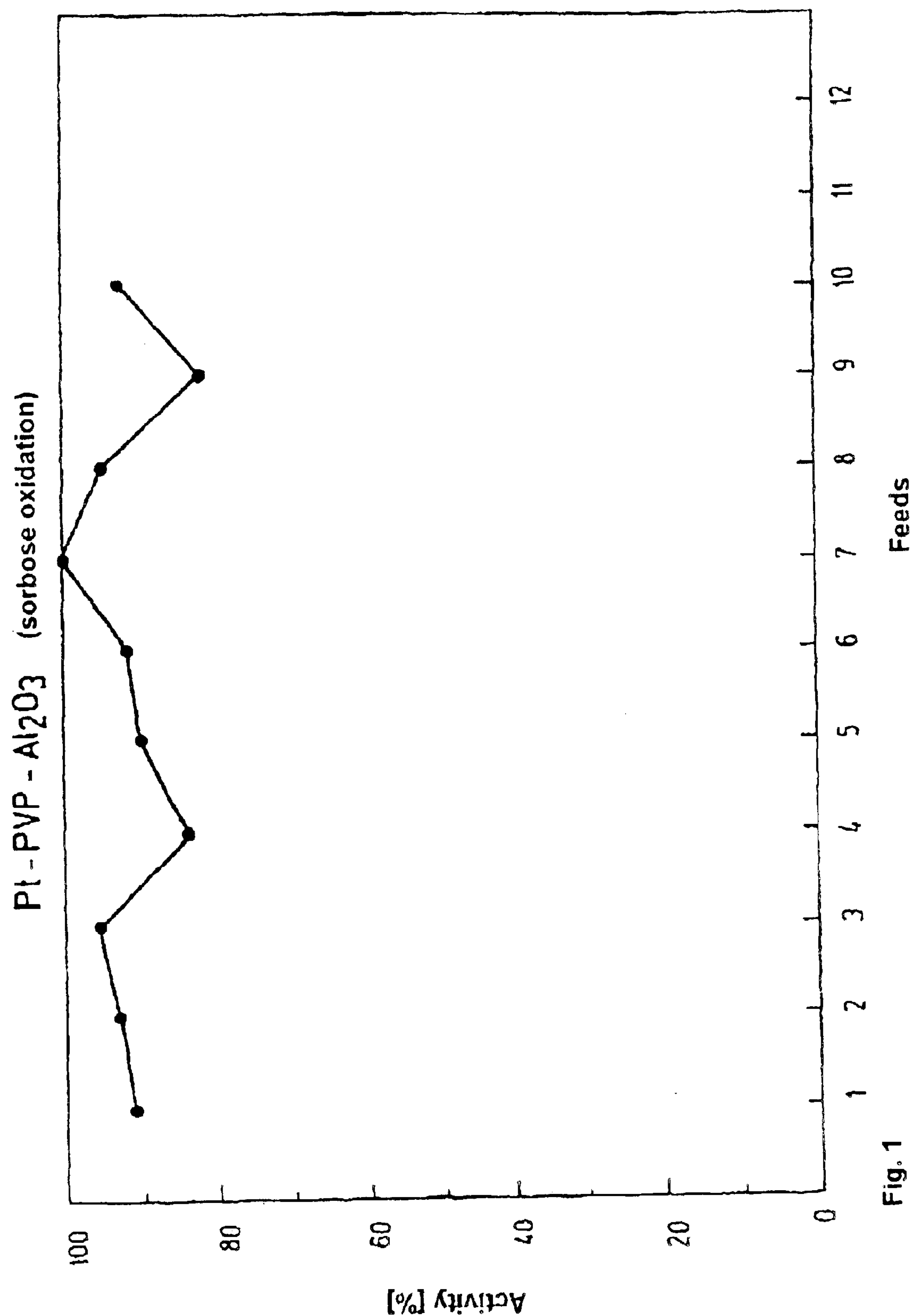

CATALYTIC PROCESS FOR THE MODIFICATION OF CARBOHYDRATES, ALCOHOLS, ALDEHYDES OR POLYHYDROXY COMPOUNDS

This application is a division under 37 C.F.R. §1.53(b) of application Ser. No. 09/936,891, filed Oct. 19, 2001, by Emine CAPAN, Marc Sascha HAHNLEIN, Ulf PRUSSE, Klaus-Dieter VORLOP and Alireza HAJI BEGLI entitled CATALYTIC PROCESS FOR THE MODIFICATION OF CARBOHYDRATES, ALCOHOLS, ALDEHYDES OR POLYHYDROXY COMPOUNDS.

The invention relates to a process for the industrial conversion of carbohydrates, alcohols, aldehydes or polyhydroxy compounds in aqueous phase.

In many industrial processes, the conversion, e.g. the oxidation, of carbohydrates, alcohols, aldehydes or polyhydroxy compounds in aqueous phase plays a decisive role and often forms the critical stage of synthesis processes.

Thus, for example, the D-gluconic acid required for many industrial applications is prepared by an oxidation of D-glucose, which is carried out as a microbial oxidation using Aspergillus niger.

A further important oxidation is the formation of 2-keto-L-gulonic acid from sorbose as intermediate step in the preparation of ascorbic acid (vitamin C). The classical Reichstein process here provides a 2-stage reaction in which, in a complex manner an L-sorbofuranose is formed, which is then oxidized to 2-keto-L-gulonic acid, for example by an electrochemical method or catalytically using nickel oxide.

The hydrogenation of reducing mono- and disaccharides with supported noble metal catalysts is described in DE 19523008 A1. For industrial production, i.e. on a large scale designed for large conversions, such catalysts are, however, unsuitable, meaning that Raney nickel catalysts generally have to be used on an industrial scale.

During the reductive amination of reducing sugars with alkylamines to give alkylaminopolyols, use is normally made of Raney nickel catalysts. One disadvantage of these catalysts is the very short service life (dissertation by M. Sch üttenhelm, 1995, TU Braunschweig), meaning that industrial conversion has hitherto been unsuccessful due to high catalyst costs. In addition, during the further work-up, dissolved or complexed Ni constituents, which permit the further use of the resulting product only through use of downstream complex and cost-intensive cleaning processes, must be taken into account.

Alternatively, the preparation of these products with supported Pd catalysts has been investigated. Here, a loss of metal was found which, firstly, considerably reduced the activity of the catalyst and, because of the economic considerations, prevents its use (dissertation by R. Cartarius, 1999, TU Darmstadt).

It is therefore in principle known, e.g. from EP 0 201 957 A2, WO 97/34861, U.S. Pat. No. 5,643,849 or tetrahedron letters 38 (1997), 9023–9026, to carry out such reactions, in particular oxidations, catalytically, in particular using noble metal catalysts, mild reaction conditions with regard to the pH and the reaction temperature being made possible. Particularly suitable catalyst metals here are platinum, but also palladium and possibly rhodium, all noble metals in principle being suitable, taking into consideration their activity and their oxygen tolerance.

The industrial use of the theoretically possible catalytic oxidation has, however, hitherto failed due to deactivation phenomena of the catalysts (cf. Mallat, Baiker 'Oxidation of alcohols with molecular oxygen on platinum metal catalysts aqueous solutions' in Catalysis Today 19 (1994), pp. 247–248). The deactivation of the catalysts is attributed here to the formation of catalyst poisons, an overoxidation of the noble metal surface and to a surface corrosion and restructuring of the noble metal. Since some of the deactivation effects of the catalyst are irreversible and cannot therefore be rectified by a regeneration, the industrial application fails due to the low service life of the catalysts and the high use of noble metal material required therewith, which makes the process uneconomical. The metal detachment which arises because of the deactivation effects causes not only high costs for the noble metal used, but also leads to contamination of the catalytically prepared product.

A proposed use of noble metal catalysts provided with promoter metals has produced a certain reduction in the irreversible deactivation effects, but still falls a long way short of making catalytic oxidation processes economically competitive with processes used hitherto.

The serious deactivation effects for carrying out an oxidation reaction have therefore led to the use of noble metal catalysts in practice only for carrying out reactions which are not very aggressive with regard to deactivation, in particular for hydrogenation reactions. For the further development of the catalysts for this purpose, enlargement of the catalyst surface by the formation of fine noble metal particles has been carried out by preparing the catalyst from a colloid. The particles are separated from one another and prevented from caking by providing the colloid with a suitable polymer such that the particles are surrounded by a polymer sheath. In this connection, attempts have also been made to reduce the susceptibility of the metal particle surfaces toward deactivation, for example by catalyst poisons. For this reason, for hydrogenation reactions of small molecules in which the reaction proceeds without diffusion limitation, metal catalysts have been used which have been formed from polymer-protected Pt or Pd particles.

For example, Chem. Ing. Technik 69 (1997), 100–103 discloses supported palladium catalysts in millimeter-sized gelatinous polymer networks for reducing nitrite. Nitrite is a very small molecule in which the reduction proceeds without diffusion limitation. Hydrogenation reactions with metal catalysts which have been formed from polymer-protected Pt or Pd particles are not disclosed in the prior art for the conversion of relatively large molecules, such as, for example, carbohydrates.

To ensure uniform distribution of the particles, it has also been proposed to surround the particles with surfactants in order to achieve a uniform distribution upon application to a support. In this technology, however, the surfactant sheath is dissolved following uniform distribution of the particles in order to achieve the catalyst effect, meaning that the sole function of the surfactant is to achieve uniform distribution.

It has also been proposed to form polymer-protected particle catalysts as bimetal or even trimetal catalysts. While the combination of noble metals serves as a selectivity control, the combination of noble metal with one or two promoter metals is successful in reducing the deactivation of the catalysts. As a result, perspectives for a practical application of a catalytic process have been opened up for the hydrogenation reaction and possibly other reducing reactions. Oxidation, which is significantly more aggressive with regard to deactivation of the catalyst, has not been investigated further in this respect due to the existing unpromising situation.

For the reactions of the generic type, recourse must therefore be further made to the known processes which are aggressive with regard to environmental influences or can only be controlled by very involved means, although considerable efforts have been made to arrive at processes which are simpler and proceed under milder reaction conditions.

Starting from the endeavor to provide an industrially applicable process for the conversion, in particular oxidation, hydrogenation or reductive amination, of carbohydrates, alcohols, aldehydes or polyhydroxy compounds in aqueous phase, which proceeds under milder reaction conditions, it is envisaged according to the invention that the conversion be carried out catalytically using a metal catalyst formed from polymer-stabilized nanoparticles.

The present invention is based on the finding, which is completely surprising and unexpected for the specialist world, that metal catalysts formed from polymer-stabilized nanoparticles are not deactivated during the catalytic conversion, in particular oxidation, hydrogenation or reductive amination, of carbohydrates, alcohols, aldehydes or polyhydroxy compounds in aqueous phase, provided the stabilizing interaction between polymer and nanoparticles is retained. In this connection, it is not necessary according to the invention that a promoter metal is added to the noble metal catalyst, even if this is naturally self-evidently possible in this process according to the invention. It is also surprising for the person skilled in the art that the known metal catalysts formed from polymer-protected particles for hydrogenation reactions for large molecules, such as carbohydrates and others, can be used, for which the person skilled in the art would have expected a diffusion limitation. The catalytic conversion of carbohydrates with these catalysts surprisingly proceeds despite the polymer matrix surrounding the active centers with high reaction rates and selectivities. The person skilled in the art would have expected that, compared with the known reactions with nitrite, the large carbohydrate molecules would be available for a reaction only to a limited extent due to the polymer matrix surrounding the active center or due to diffusion limitation. However, it could be shown that even the large di- and oligosaccharide molecules can advantageously be converted using the catalyst system according to the invention.

The present invention relates in particular to processes for the industrial conversion of starting materials, chosen from the group consisting of alcohols, aldehydes and/or polyhydroxy compounds, such as carbohydrates, carbohydrate derivatives, starch hydrolysates, in particular mono-, di- or trisaccharides, in aqueous phase, where the conversion is carried out catalytically using a metal catalyst formed from polymer-stabilized nanoparticles. It may be provided also to jointly convert mixtures of said starting materials.

In a preferred embodiment of the present invention, the conversion is an oxidation of said starting materials, carbohydrates, for example glucose, sorbose, sucrose, maltose, lactose, starch hydrolysates and/or isomaltulose preferably being oxidized to the corresponding carbohydrate acids. Because of the very aggressive conditions during oxidations, the long-term stability observed according to the invention and the metal leaching which does not arise in this embodiment are particularly surprising.

In a further embodiment, the conversion is a reduction, in particular a hydrogenation, reducing sugars, such as, for example, glucose, fructose, xylose, sorbose, isomaltose, isomaltulose, trehalulose, maltose and/or lactose, being hydrogenated to give the corresponding sugar alcohols. In this way, it is possible, for example, to obtain isomalt, 1,1-GPM (1-O-α-D-glucopyranosyl-D-mannitol) or 1,6-GPS (6-O-α-D-glucopyranosyl-D-sorbitol) enriched mixtures from isomaltulose. Such enriched mixtures are described in DE 195 31 396 C2.

In a further embodiment, the industrial conversion of said starting materials can be a reductive amination, preference being given to reductively aminating reducing sugars, in particular glucose, fructose, xylose, sorbose, isomaltose, isomaltulose, trehalulose, maltose and/or lactose.

In a preferred embodiment, the metal catalyst is a catalyst which essentially consists of noble metal or comprises the latter, where the noble metal can, for example, be platinum, palladium, rhodium and/or ruthenium. However, the metal catalyst can also be a catalyst which essentially consists of a base metal or comprises the latter, where the base metal can, for example, be copper and/or nickel.

In connection with the present invention, the conversion takes place in aqueous phase, the conversion preferably taking place at a temperature of from 35–120° C. and a pH of from 5 to 12.

In connection with the present invention, a polymer-stabilized nanoparticle is understood as meaning a metal particle around which a polymer sheath is formed, where the total diameter of the polymer-coated metal particle, as metal particle core plus sheath, is preferably in a range from 3 to 200 nanometers.

The invention provides in a particularly preferred manner that the alcohols, aldehydes or polyhydroxy compounds to be reacted, in particular carbohydrates, carbohydrate derivatives or the like are converted in aqueous solution, concentrations of from 0.1 to 60% being preferred. For example, the glucose may be present in the form of glucose syrup.

In particular, in a further preferred embodiment, it may be provided to pass the products mentioned above converted according to the invention during the oxidation following their conversion to a product solution to an electrodialysis, and in so doing to remove and obtain the products from the resulting product solution. A particularly preferred procedure of this type is suitable, for example, for the preparation of monooxidized carbohydrates or carbohydrate derivatives and primary alcohols. Separating off the oxidation products by means of electrodialysis, for example as described in EP 0 651 734 B1, leads to virtually pure products being obtained.

The process according to the invention can thus be coupled in a preferred manner with a process and the appertaining equipment according to EP 0 651 734 B1 in order to obtain the desired products in a particularly pure form by means of electrodialysis. The teaching of EP 0 651 734 B1 is incorporated in its entirety into the disclosure content of the present teaching with regard to the electrodialysis separation described therein, and protection is also sought therefor.

If the catalyst particles according to the invention are continually used repeatedly, it must be taken into consideration that the polymer sheath around the nanoparticles is detached or consumed. According to the invention, it is therefore particularly preferred if the polymer stabilizing the nanoparticles is added to the aqueous phase continuously or at suitable time intervals in order, in this way, to ensure that the effective polymer sheath around the nanoparticles is retained.

In the process according to the invention, the nanoparticles can be immobilized in a manner known per se on a support material, i.e. supported, the support material used preferably being a porous material in continuous form or in powder form, or the polymer-stabilized nanoparticles are immobilized in a gel structure.

Suitable immobilization materials with the help of adsorption are, in particular: $Al_2O_3$, $SiO_2$, $TiO_2$, $ZrO_2$, activated carbon, polymer latex, polystyrene latex, polyacrylamide gel, Deloxan (alkylsulfonic acid polysiloxane, aminoethyl Bio-Gel P-150. Inclusion immobilization can take place in a preferred embodiment in alginates, polyvinylalcohol, polyurethanes or the like.

If, in one embodiment of the invention, supported catalysts immobilized as described above are used, the polymer-stabilized and/or supported nanoparticles according to the invention can preferably be homogeneously or inhomogeneously distributed in gels, particularly hydrogels, or else be localized on the surface. As well as the support materials aluminum oxide, silicon dioxide and/or titanium dioxide, also suitable for this purpose are activated carbon, alumosilicates and ion exchange resins or the like.

Finally, in a further embodiment, membrane arrangements are also possible in which the active component, i.e. the polymer-stabilized nanoparticles, optionally also in supported form, are applied to or between membranes (for example hollow fibers, diffusion membranes, porous membranes and flat membranes).

In a preferred embodiment, suitable polymers for protecting and coating the nanoparticles are numerous homopolymers, copolymers and, in particular, block copolymers and graft copolymers. Particular mention may be made of polyvinyl pyrrolidones and suitable derivatives, polyvinyl alcohol, polyacrylic acid, poly(2-ethyl-2-oxazoline), poly(2-hydroxypropyl methacrylate), poly(methyl vinyl ether-co-maleic anhydride), polymethacrylic acid, poly(1-vinylpyrrolidone-co-acrylic acid), poly(styrenesulfonic acid), poly(2-acrylamido-2-methyl-1-propanesulfonic acid), poly-(vinylphosphonic acid), polydiallyldimethylammonium chloride (PDADMAC), polymethacrylamidopropyltrimethylammonium chloride, poly (3-chlorohydroxypropyl-2-methacryloxyethyldimethylammonium chloride).

The catalysts according to the invention can be used, in a preferred embodiment, also as colloids/clusters, the active component being in the form of free, i.e. not immobilized, colloids or clusters. The largest arrangement of these colloids/clusters is, according to the invention, in the nanometer range, i.e. in a range from 1 nm to 20 nm. It is only essential that the colloid particles and clusters are surrounded by a protecting polymer sheath.

The catalysts can be designed according to the type of catalyst and the reactor in question, for example as spheres, beads, cylinders, hollow cylinders, meshes, powders, pressed articles, granules, hollow spheres, fibers and films. The process itself can be used in plants which operate continuously, semicontinuously or else batchwise. Depending on the catalyst used, suitable reactors are, for example, fixed-bed reactors, reactors with expanding fixed beds, moving-bed reactors, fluidized bed reactors, stirred-bed reactors, stirred tank reactors and membrane reactors. These systems can be operated with or without catalyst and/or liquid recycling. These systems can, if necessary, also be provided with suitable internals for catalyst retention, for example with cyclones, filters and membranes.

Further advantageous embodiments arise from the dependent claims.

The invention is illustrated in more detail by reference to the examples below and the appertaining figures.

The figures show

FIG. 1: Measurement results for the oxidation of sorbose using a catalyst used according to the invention, FIG. 2: Measurement results for the oxidation of sorbose using a comparison catalyst, FIG. 3: Measurement results for the oxidation of sorbose using a catalyst used according to the invention, FIG. 4: Measurement results for the oxidation of glucose using a catalyst used according to the invention, FIG. 5: Measurement results for oxidation of sucrose using a catalyst used according to the invention and a comparison catalyst, FIG. 6: Measurement results for the reductive amination of isomaltulose using a catalyst used according to the invention and a comparison catalyst, FIG. 7: Measurement results for the hydrogenation of isomaltulose using a catalyst used according to the invention and a comparison catalyst.

EXAMPLE 1

Preparation of PVP-stabilized Platinum Colloids 3.27 g of polymer, namely polyvinylpyrrolidone (PVP), are dissolved in 33 ml of methanol, it possibly being necessary to gently heat the solution so that the polymer dissolves completely. Following dissolution of the polymer, 398.2 mg (0.769 mmol) of hydrogen hexachloroplatinate (IV) hydrate ($H_2PtCl_6.6H_2O$) (platinum content 150 mg) and 291.6 mg (7.29 mmol) of NaOH are added thereto and the mixture is boiled under reflux. The solution also turns yellow during this operation upon the addition of hydrogen hexachloroplatinate (IV) hydrate. Following reduction, the mixture is boiled under reflux for a further 60 minutes. The reduction takes place suddenly only after boiling for about 30 minutes. The reduction is also evident here from the formation of a brown-black colloidal sol. After the sol has cooled, the unreacted alcohol is removed dialytically. During the dialysis, the colloidal sol is continuously circulated by pump through the intracapillary volume of a hollow fiber dialysis module (Fresenius model F5 HPS) in countercurrent to deionized water in the extracapillary volume. During dialysis, all of the colloidal sol is retained.

EXAMPLE 2

Supporting the Pt Colloid on $Al_2O_3$ 4.69 g of $Al_2O_3$ (HL 1000) in the form of highly porous particles are added to a colloidal solution comprising 50 mg of Pt. 1.15 ml of formic acid are then added and the mixture is stirred overnight. The solution becomes clear over the course of time. The reaction mixture is filtered over a G4 frit. The solid is washed first with methanol and then with distilled water and dried in a drying cabinet.

EXAMPLE 3

Sorbose Oxidation

To determine the sorbose degradation activity, the reactor is filled with 150 ml of catalyst suspension. Prior to the feeds, the reaction suspension is gassed for 30 minutes with hydrogen in order to expel other gases, primarily oxygen, from the reaction solution and in order to activate the catalyst. To strip the dissolved hydrogen from the reaction suspension, the solution is gassed with nitrogen for about 15 minutes. Under nitrogen blanketing, 7.5 g of sorbose are added to the solution, and the mixture is heated to a reaction temperature of 50° C. The pH is then adjusted to 7.3. After the reaction suspension has reached 50° C., it is then gassed with oxygen, i.e. the reaction is thereby started, the gassing rate at the start being very high so that rapid saturation of the reaction suspension is achieved. After complete saturation (about 95%) has been achieved, the gassing rate is reduced. The degree of saturation is monitored using the oxygen electrode, and the gassing rate is increased again where necessary so that the reaction remains saturated over the entire course of the reaction. The reaction time was 24 hours per feed. The catalyst was then subjected to the regeneration treatment mentioned and is then prepared for the next feed.

EXAMPLE 4

Comparative Experiment

Figure 2:
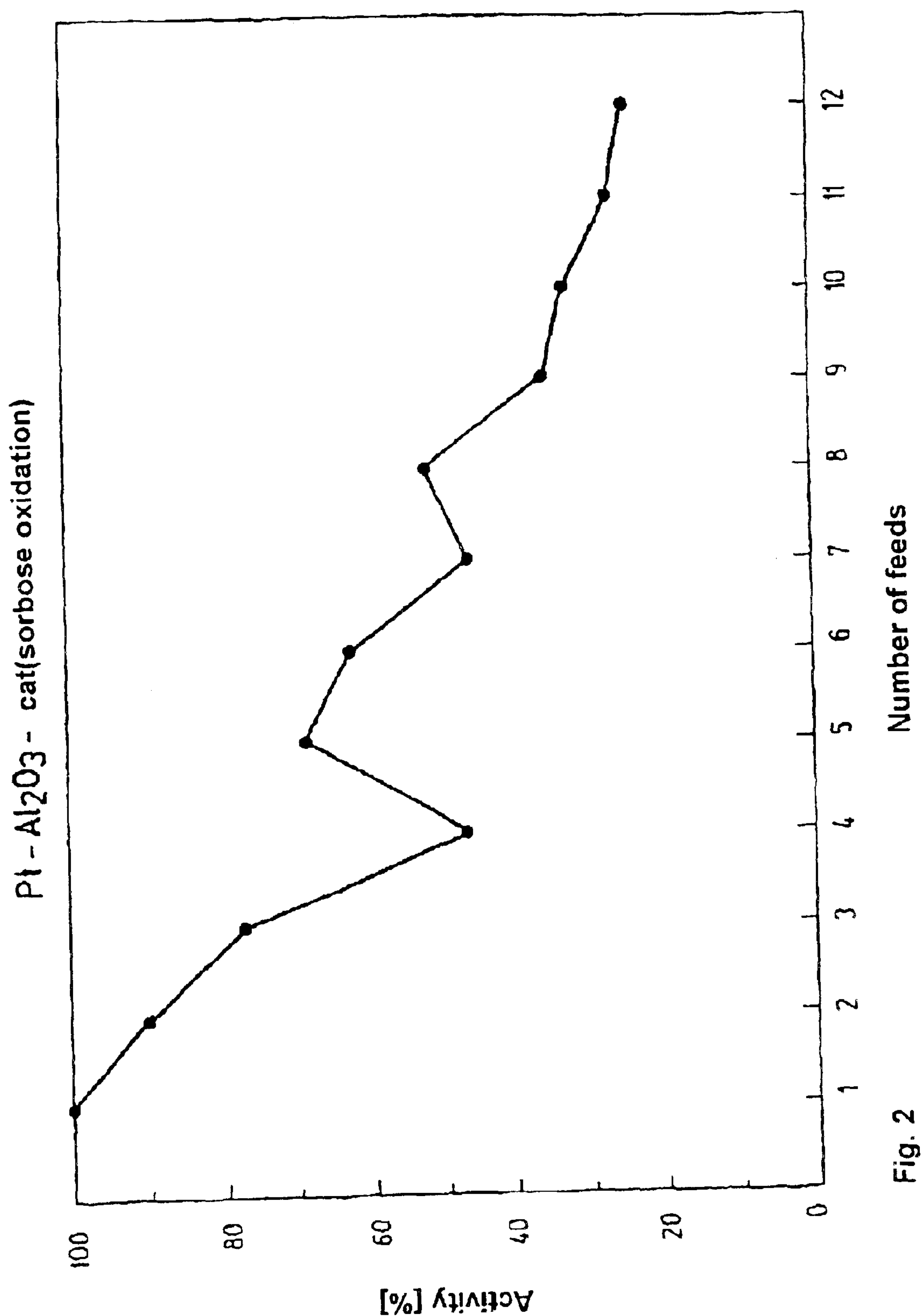

For the sorbose oxidation shown in example 3, the polymer-protected platinum colloid catalyst prepared according to example 1 and 2 has been investigated with regard to its activity in repeated reaction runs. The measurement results obtained therein are shown in FIG. 1 and show that the activity of the catalyst remains virtually unchanged over many feeds (of 24 hours in each case), while a traditional platinum catalyst on $Al_2O_3$ has an activity which is reduced to 20 to 30% following comparable feeds, as FIG. 2 shows. Using atomic absorption spectroscopy, it has been established that the traditional platinum catalyst had lost 28% platinum after just 6 feeds, while the catalyst according to the invention had no losses.

EXAMPLE 5

Figure 3:
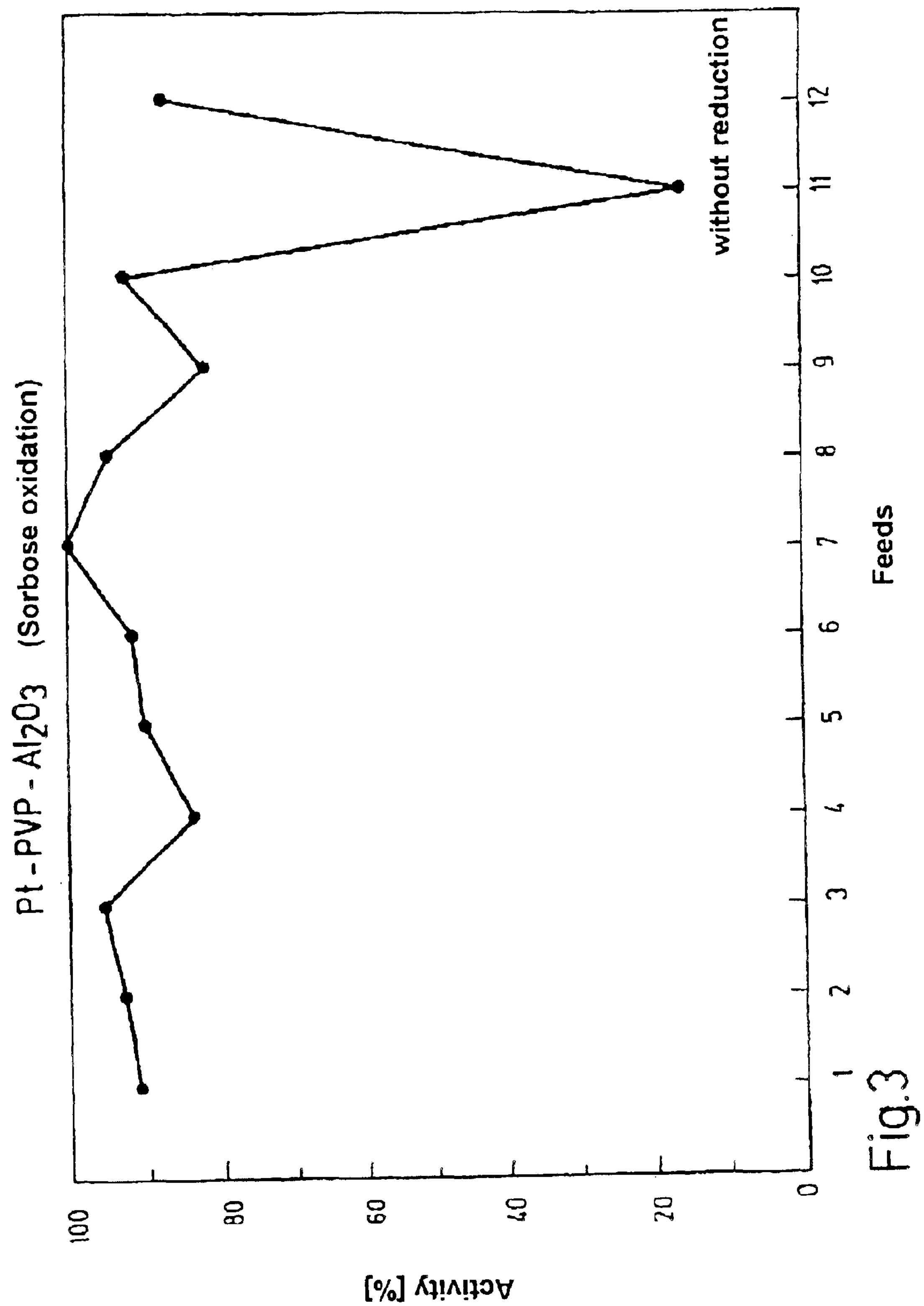

FIG. 3 illustrates the activity course for a catalyst according to the invention analogous to FIG. 1, where the regenerating gassing with hydrogen according to example 3, which has been carried out in other respects, has been omitted, as a result of which the activity has been considerably reduced during the eleventh feed. However, by subsequently carrying out gassing with hydrogen, the original activity is restored, as is evident at the twelfth feed according to FIG. 3. Deactivation without regeneration treatment is therefore reversible.

EXAMPLE 6

Glucose Oxidation

Figure 4:
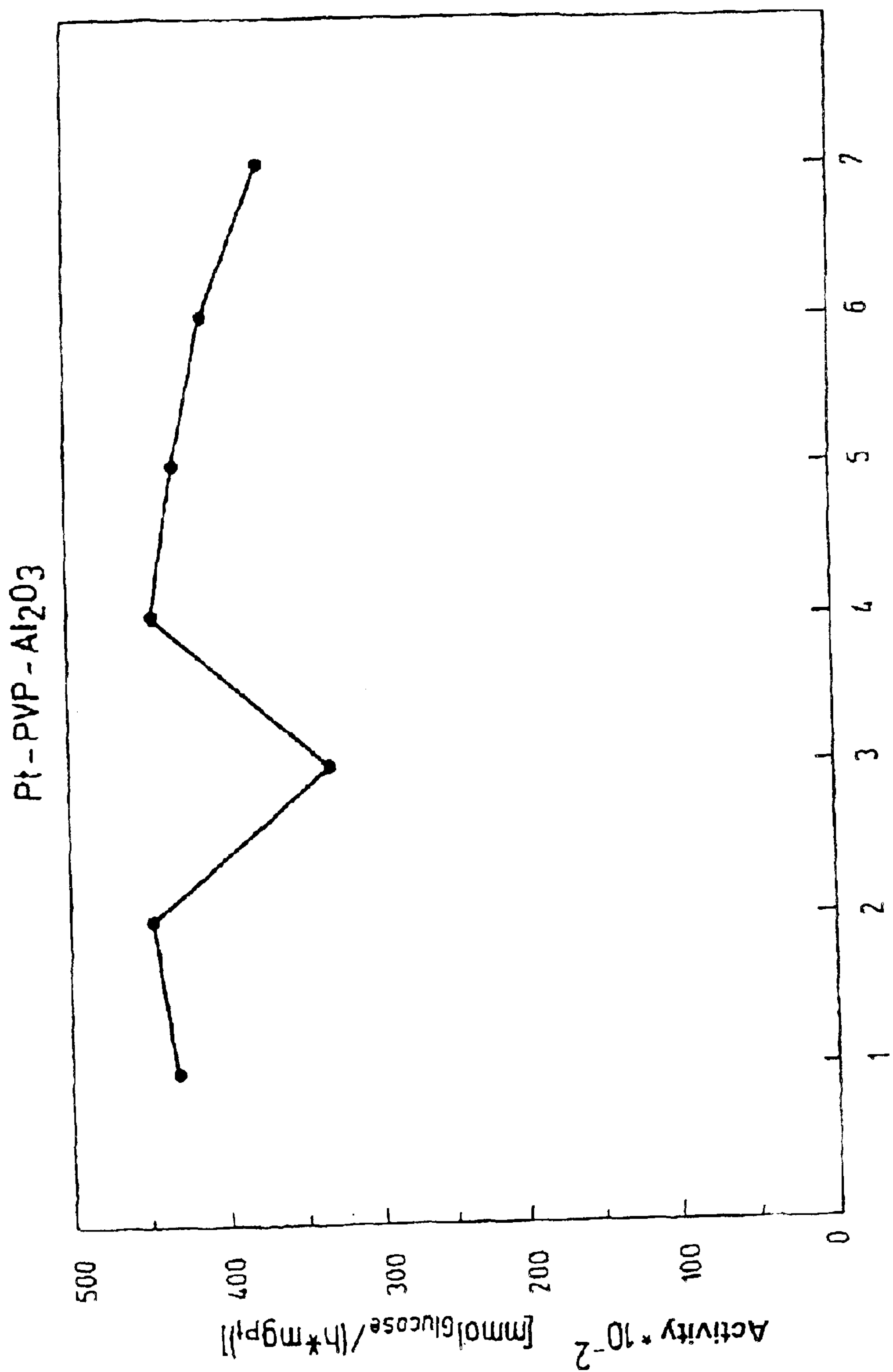

To determine the glucose degradation activity, the reactor is filled with 100 ml of catalyst suspension. Prior to the feeds, the reaction suspension is gassed with nitrogen for 15 minutes in order to expel other gases, primarily oxygen, from the reaction solution. Under nitrogen blanketing, 10 g of glucose are added to the solution, and the mixture is heated to a reaction temperature of 50° C. The pH is then adjusted to 9.5. After the reaction suspension has reached 50° C., it is then gassed with oxygen, i.e. the reaction is thereby started, the gassing rate at the start being very high in order to achieve rapid saturation of the reaction suspension. After complete saturation (about 95%) has been reached, the gassing rate is reduced. The degree of saturation is monitored using the oxygen electrode, and the gassing rate is increased again where necessary so that the reaction remains saturated over the entire course of the reaction. FIG. 4 shows that the activity of the catalyst at worst decreases slightly after a few feeds of 4 hours each, while traditional catalysts are virtually unusable after no more than 4 feeds because the activity has dropped to 20% or below.

EXAMPLE 7

Preparation of Polymer-stabilized Metal Colloids

TABLE 1

Qualitative composition of catalysts 1 to 5

| | Active metal | Support | Stabilizing polymer | Type of conversion |
|---|---|---|---|---|
| Catalyst 1 | Pt | $Al_2O_3$ | Polyvinyl-pyrrolidone | Oxidation |
| Catalyst 2 | Pd | $TiO_2$ | Poly(1-vinyl-pyrrolidone)-co-acrylic acid | Reductive amination |
| Catalyst 3 | Ru | $Al_2O_3$ | Polyvinyl-pyrrolidone | Hydrogenation |
| Catalyst 4 | Cu | Activated carbon | Polyvinyl-pyrrolidone | Hydrogenation |
| Catalyst 5 | Ni | $TiO_2$ | Polymethacryl-amidopropyl-trimethyl-ammonium chloride | Hydrogenation |

The polymer-stabilized metal colloids were prepared analogously to example 1. The composition of the catalyst is given in table 1. The use amount of the polymer used in each case was here initially kept constant. The amount of noble metal acids or metal salts used was chosen such that, following theoretical complete conversion, a catalytically active metal content of 150 mg can be assumed. Table 2 shows the raw materials and amounts for the preparation of the catalysts.

TABLE 2

Quantitative composition of catalysts 1 to 5

| | Active metal | Starting component | Amount of starting component in mg | Amount in mmol |
|---|---|---|---|---|
| Catalyst 1* | Pt | $H_2PtCl_6 \cdot 6\ H_2O$ | 398.2 | 0.769 |
| Catalyst 2 | Pd | $PdCl_2$ | 249.9 | 1.41 |
| Catalyst 3 | Ru | $RuCl_3$ | 307.9 | 1.48 |
| Catalyst 4 | Cu | $CuCl_2$ | 319.7 | 2.36 |
| Catalyst 5 | Ni | $Ni(NO_3)_2$ | 466.9 | 2.56 |

*as used for the oxidation of sorbose in example 3

The catalysts were supported analogously to the procedure given in example 2.

EXAMPLE 8

Oxidation of Sucrose

The oxidation of sucrose using catalyst 1 is carried out in accordance with example 3.

The reaction temperature here is 40° C., and an electrodialysis unit is used to continuously separate off the oxidation products (described in detail in the dissertation by M. Schüttenhelm, TU Braunschweig and in EP 0 651 734 B1) The unit was operated for 10 days and produced the following product spectrum:

1-O-(β-D-fructosylfuranuronyl)-α-D-glucopyranoside: 36±3%

2-O-(α-D-glucopyranosyl)-β-D-glucofuranonic acid: 37±3%

1-O-(β-D-fructosylfuranosyl)-α-D-glucopyranuronide: 10±2%

Other products which could not be characterized further: 5±2%

The activity of the catalyst was virtually constant over 10 days.

As a comparison, a non-polymer-stabilized commercially available catalyst containing Pt on an activated carbon support and having a metal content of 1% by weight was tested and produced the following product spectrum:

1-O-(β-D-fructosylfuranuronyl)-α-D-glucopyranoside: 37±3%

2-O-(α-D-glucopyranosyl)-β-D-glucofuranonic acid: 36±3%

1-O-(β-D-fructosylfuranosyl)-α-D-glucopyranuronide: 10±2%

Other products which could not be characterized further: 13±2%

Figure 5:
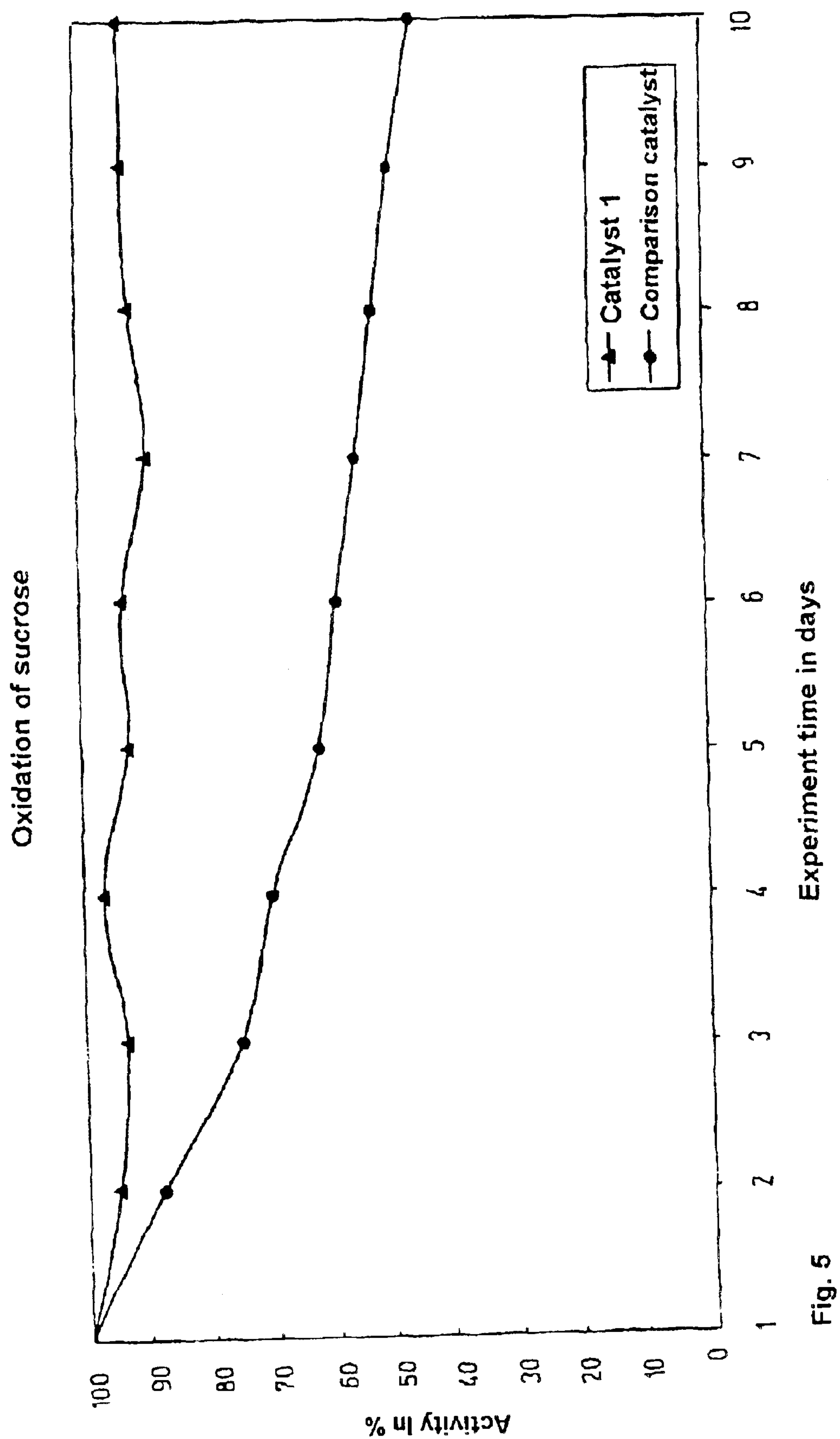

As well as the desired monosucrose carboxylic acids, this comparison catalyst produced a considerably higher proportion of byproducts, as FIG. 5 shows. Even after the third day it was possible to observe a continuous decrease in catalyst activity.

EXAMPLE 9

Reductive Amination of Isomaltulose (palatinose) in the Suspension Process

The investigations for the reductive amination were carried out in a high-pressure autoclave in a slurry process using catalyst 2 (cf. Ex. 7) (5 g).

The catalytic hydrogenations were carried out in a laboratory high-pressure autoclave with the following operating data:

Autoclave 750 ml high-pressure autoclave, thermostatable; max. operating pressure: 15 Mpa (BERGHOF, Eningen)

speed-controlled, inductively operated stirrer internal temperature measurement by PT 100 resistant thermometer manual sampling needle valve Thermostat Compact low-temperature thermostat RKS 20 D with external control unit (LAUDA, Lauda-Königshofen)

Introduction of Hydrogen

Removal from cylinders via pressure-reducing valves:

<10 Mpa: flushing unit; 15 Mpa: reaction connection

Amination with n-dodecylamine 50 g (0.139 mmol) of palatinose monohydrate ($M_r$ [$C_{12}H_{22}O_{11}H_2O$]=360.31 g/mol) were dissolved in a mixture of 180 ml of water and 55 ml of 2-propanol in a thermostatable 55 ml double-walled flask, and cooled to 10° C. A solution of 7.36 g (0.040 mol) of n-dodecylamine ($M_r$[$C_{12}H_{27}N$]=185.35 g/mol) in 120 ml of water and 70 mol of 2-propanol was slowly added dropwise thereto, and the mixture was stirred well for 1 h. The resulting osylamine reaction solution was transferred to the heated autoclave, and mixed with the catalyst, then flushed rapidly three times with hydrogen and hydrogenated for 24 h at 50 bar and 70° C. After cooling to room temperature, the catalyst was filtered off and the crude product solution was carefully concentrated on a rotary evaporator at 38° C. in a water-jet vacuum. The residue was then purified.

It was found that the hydrogen partial pressure during the hydrogenation should, in a preferred embodiment, be at least 30 bar in order to suppress undesired secondary reactions. It is of course also possible to carry out the hydrogenation at 180 bar or above. The experiments were all carried out at 50 bar and a temperature of 70° C.

The plant was operated batchwise for 10 days and filled with new starting material solution every 24 hours. The catalyst was not changed during this time. As a comparison, a non-polymer-stabilized catalyst (1% Pd on $TiO_2$) was tested. The activity was assessed by determining the isomaltulose conversion in each case after 24 hours. At the start, the conversion was virtually quantitative for the two catalysts (red. substances <0.1%, therefore below the detection limit); this value was chosen, as 100%, to be the reference parameter for the evaluation of the experimental series.

Figure 6:
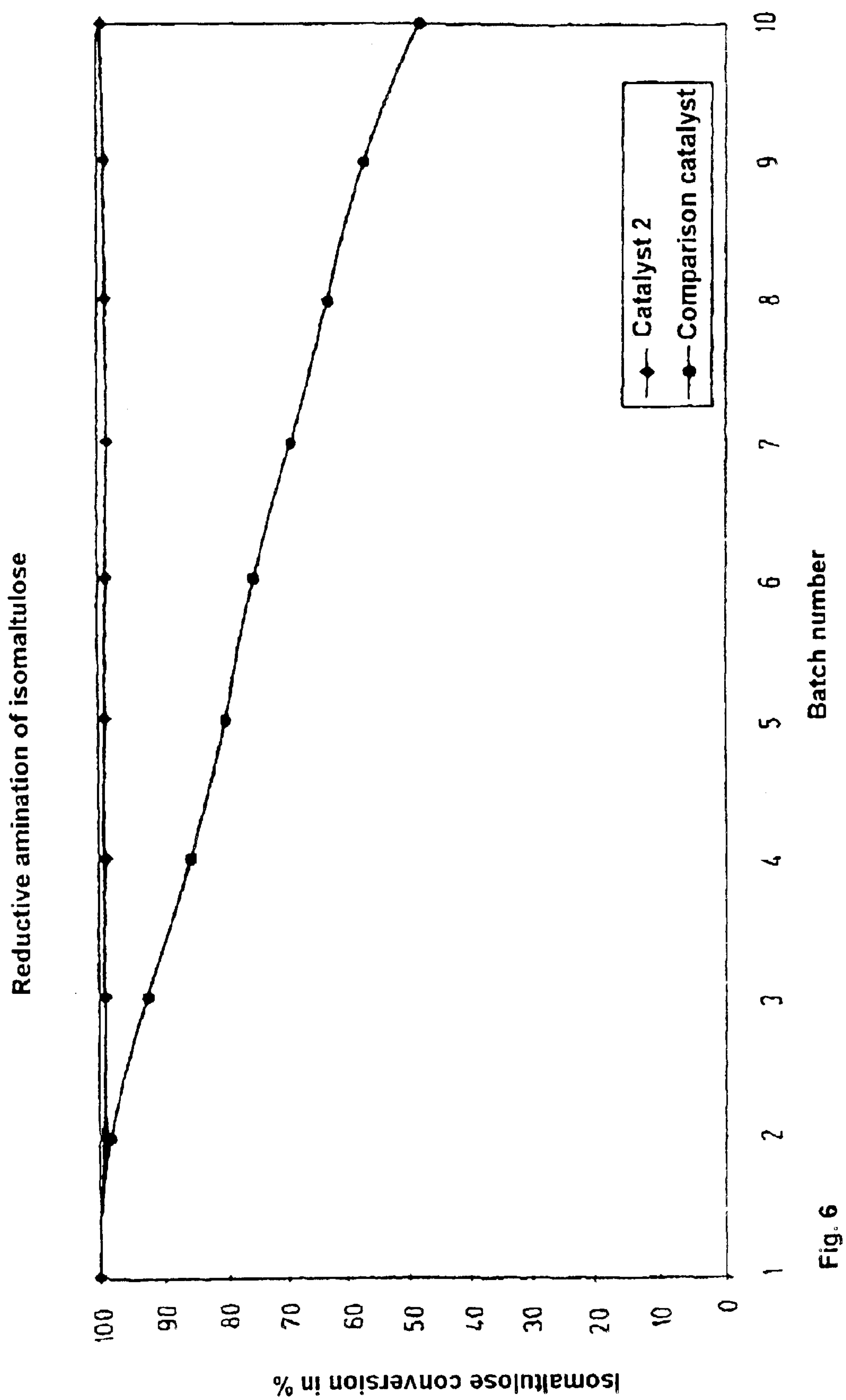

The results are shown in FIG. 6.

The non-polymer-stabilized support loses 15% of its reactivity after just the third day in this reaction; the reactivity of the polymer-stabilized catalyst remains virtually unchanged throughout the investigated period.

EXAMPLE 10

Hydrogenation Experiments

Within the scope of the investigations, the suitability of polymer-stabilized catalysts for hydrogenation reactions was investigated.

In each case, 5 g of catalysts 3–5 were prepared and tested in the autoclave system described above with the sugar isomaltulose. For this, 500 ml of isomaltulose solution with a dry-substance content of 30% were in each case introduced into the autoclaves, and 5 g of the catalyst were added. As comparison catalyst, an Ni/$SiO_2$-based standard catalyst was used. The autoclave was sealed and flushed three times with nitrogen to remove the oxygen. The subsequent 10 batch hydrogenations for each catalyst were carried out at the following parameter settings:

| | |
|---|---|
| Reaction temperature: | 70° C. |
| Hydrogen partial pressure: | 150 bar |
| Stirrer speed: | 700 rpm |
| Reaction time: | 24 h |

Figure 7:
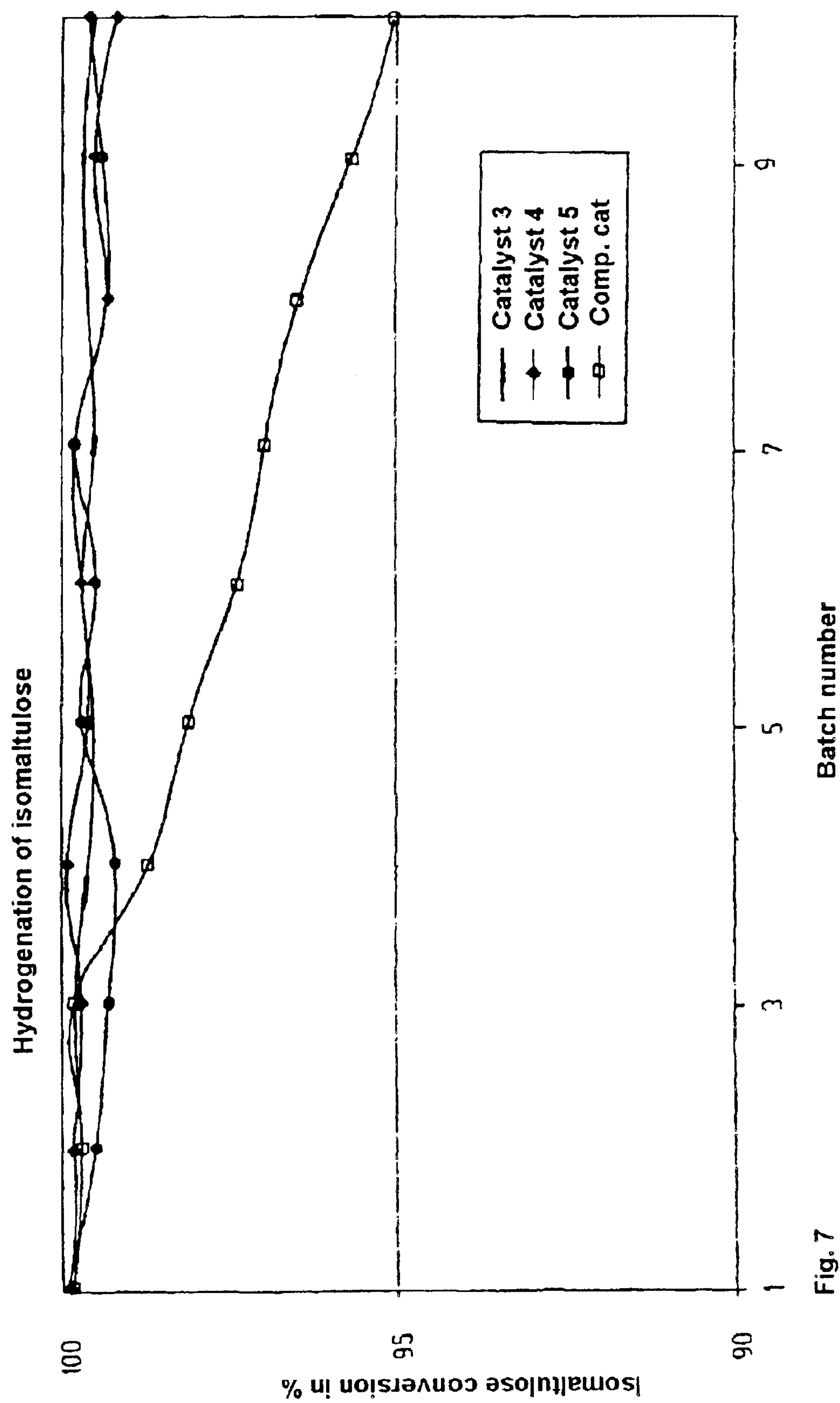

The hydrogenation of isomaltulose produces, as main products, a polyol isomer mixture consisting of 6-O-α-D-glucopyranosyl-D-sorbitol (1,6-GPS) and 1-O-α-D-glucopyranosyl-D-mannitol (1,1-GPM). The activity was assessed by determining the isomaltulose conversion after 24 hours. FIG. 7 shows that in the case of catalysts 3 to 5, no reduction in reactivity is observed during the period of investigation, while in the case of the comparison catalyst, a decrease in reactivity is observed even from the 5th hydrogenation.

Depending on the metal used and support for the catalysts used, it is possible to selectively control the quantitative ratio with regard to the 1,6-GPS and 1,1-GPM proportion of the product solutions. As table 3 shows, the selectivity of the hydrogenation reaction can be influenced through the choice of catalyst in such a way that targeted preparation of an appropriately 1,6-GPS and 1,1-GPM enriched product solution is possible.

TABLE 3

Selectivity of the hydrogenation reaction

| Catalyst | Selectivity |
|---|---|
| Catalyst 3 | 1,6-GPS-selective |
| Catalyst 4 | 1,1-GPM-selective |
| Catalyst 5 | equimolar ratio |
| Comparison catalyst | equimolar ratio |

The examples given demonstrate that, despite varying combinations of different metals, polymers and supports, a large number of principally identical catalysts can be prepared which have the common feature that, particularly in an aqueous medium, they have a significantly higher ability with regard to adhesion and loading of the active metal component and thus longer service lives than traditionally used catalysts.

What is claimed is:

1. A process for the catalytic conversion of carbohydrates, alcohols, aldehydes or polyhydroxy compounds in aqueous phase, which comprises carrying out the conversion using polymer-coated metal particles with a total diameter in a range from 3–200 nm as a metal-catalyst wherein the conversion is an oxidation, wherein said process comprises the steps of:

mixing the compound to be oxidized with the nanoparticles in an aqueous solution, introducing oxygen, conducting the oxidation, and separating off the oxidation products obtained.

2. The process as claimed claim 1, wherein at least one of glucose, fructose, sorbose, sucrose, isomaltulose is oxidized.

* * * * *